United States Patent
Sinclair et al.

(10) Patent No.: US 9,934,937 B2
(45) Date of Patent: Apr. 3, 2018

(54) PROTEIN LAYERS AND THEIR USE IN ELECTRON MICROSCOPY

(71) Applicant: Isis Innovation Limited, Oxford (GB)

(72) Inventors: John Charles Sinclair, Oxford (GB); Martin Edward Mäntylä Noble, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 136 days.

(21) Appl. No.: 14/489,108

(22) Filed: Sep. 17, 2014

(65) Prior Publication Data

US 2015/0053856 A1    Feb. 26, 2015

Related U.S. Application Data

(63) Continuation of application No. 12/602,248, filed as application No. PCT/GB2008/001437 on Apr. 23, 2008, now abandoned, which is a continuation-in-part of application No. 11/807,922, filed on May 30, 2007, now abandoned, which is a continuation-in-part of application No. 10/530,795, filed as application No. PCT/GB03/04306 on Oct. 8, 2003, now Pat. No. 7,989,591.

(30) Foreign Application Priority Data

Oct. 8, 2002   (GB) .................................... 022323.7

(51) Int. Cl.
| | |
|---|---|
| C07K 14/24 | (2006.01) |
| H01J 37/22 | (2006.01) |
| C07K 14/00 | (2006.01) |
| C07K 14/36 | (2006.01) |
| C07K 14/47 | (2006.01) |
| C07K 14/715 | (2006.01) |
| C07K 19/00 | (2006.01) |
| H01J 37/20 | (2006.01) |
| H01J 37/295 | (2006.01) |
| G01N 33/68 | (2006.01) |
| H01J 37/26 | (2006.01) |

(52) U.S. Cl.
CPC .......... *H01J 37/222* (2013.01); *C07K 14/001* (2013.01); *C07K 14/24* (2013.01); *C07K 14/36* (2013.01); *C07K 14/47* (2013.01); *C07K 14/7151* (2013.01); *C07K 19/00* (2013.01); *G01N 33/6803* (2013.01); *H01J 37/20* (2013.01); *H01J 37/261* (2013.01); *H01J 37/295* (2013.01); *C07K 2319/00* (2013.01); *H01J 2237/201* (2013.01); *H01J 2237/2802* (2013.01); *H01J 2237/2803* (2013.01)

(58) Field of Classification Search
CPC ........ H01J 37/222; H01J 37/261; H01J 37/20; H01J 37/295; G01N 33/6803; C07K 14/7151; C07K 19/00; C07K 14/001; C07K 14/36; C07K 14/47; C07K 14/24
See application file for complete search history.

(56) References Cited

U.S. PATENT DOCUMENTS

| | | | |
|---|---|---|---|
| 5,597,457 A | * | 1/1997 | Craig ................. C10M 171/001 204/165 |
| 7,989,591 B2 | | 8/2011 | Sinclair |
| 2006/0173166 A1 | | 8/2006 | Sinclair et al. |
| 2008/0097080 A1 | | 4/2008 | Sinclair et al. |
| 2010/0202672 A1 | | 8/2010 | Sinclair |

FOREIGN PATENT DOCUMENTS

| | | |
|---|---|---|
| WO | WO 96/17055 A1 | 6/1996 |
| WO | WO 00/68248 A2 | 11/2000 |

(Continued)

OTHER PUBLICATIONS

Srisawat et al., Streptavidin aptamers: Affinity tags for the study of RNAs and ribonucleoproteins., RNA (2001), vol. 7, pp. 632-641.*
Schmidt et al., Molecular Interaction Between the Strep-tag Affinity Peptide and its Cognate Target, Streptavidin., JMB (1996), vol. 255, pp. 753-766.*
Haschemeyer et al., Electron Microscopy of Enzymes, Annu. Rev. Biochem. (1974), vol. 43, pp. 279-301.*
Venien-Bryan (last updated in 2002).*
Annex to Response to Communication of Feb. 10, 2006 in European Patent Application No. 03753741.2, entitled "Protein Lattice," filed on Aug. 15, 2006.
Berman, H.M., et al., "The Protein Data Bank," *Nucleic Acids Research*, 28:235-242 (2000).
Branden, et al., "Introduction to Protein Structure Second Edition," Garland Publishing Inc., New York, 1999.

(Continued)

*Primary Examiner* — Karen Cochrane Carlson
(74) *Attorney, Agent, or Firm* — Hamilton, Brook, Smith & Reynolds, P.C.

(57) ABSTRACT

Protein layers (1) repeating regularly in two dimensions comprise protein protomers (2) which each comprise at least two monomers (5), (6) genetically fused together. The monomers (5), (6) are monomers of respective oligomer assemblies (3), (4) into which the monomers are assembled to assembly of the protein layer. The first oligomer assembly (3) belongs to a dihedral point group of order O, where O equals (3), (4) or (6) and has a set of O rotational symmetry axes of order (2). The second oligomer assembly (4) has a rotational symmetry axis of order (2). Due to the symmetry of the oligomer assemblies (3), (4), the rotational symmetry axes of each second oligomer assembly (4) is aligned with one of said set of O rotational symmetry axes of a first oligomer assembly (3) with (2) protomers being arranged symmetrically therearound. Thus, an 2-fold fusion between the oligomer assemblies (3), (4) is produced and the arrangements of the rotational symmetry axes of the oligomer assemblies (3), (4) cause the protein layer to repeat regularly. The protein layer has many uses, for example to support molecular entities for biosensing, x-ray crystallography or electron microscopy.

26 Claims, 3 Drawing Sheets

(56) References Cited

FOREIGN PATENT DOCUMENTS

WO     WO 01/85962 A1     11/2001
WO     WO 2004/033487 A1     4/2004

OTHER PUBLICATIONS

Dotan, et al., "Self-Assembly of a Tetrahedral Lectin into Predesigned Diamondlike Protein Crystals," *Angew. Chem. Int. Ed.*, 38(16):2363-2366 (1999).
Drenth, "Principles of X-ray Crystallography," Springer, New York, 1995.
Ghadiri, M.R., et al., "Self-Assembling Organic Nanotubes Based on a Cyclic Peptide Architecture," *Nature*, 366(25):324-327 (1993).
Giege, et al., Crystallogenesis of Biological Macromolecules: Facts and Perspectives, *Acta Cryst.*, D50-339-350 (1994).
Hestenes, D., Point Groups and Space Groups in Geometric Algebra,Retrieved from the Internet at <http://modelingnts.la.asu.edu/pdf/crystalsymmetry.pdf>, [Retrieved on Mar. 18, 2008].
Kierzek, et al., *Biophys. Chem.*, 91:1-20 (2001).
Merriam-Webster On-line Dictionary Definition of "monomer", Retrieved from the Internet at www.merriam-webster.com, [Retrieved on Mar. 18, 2008].
Narayana, et al., The Dimerization Domain of HNF-1α: Structure and Plasticity of an Intertwined Four-Helix Bundle with Application to Diabetes Mellitus, *J. Mol. Biol.*, 310:635-658 (2001).
Ngo J.T., et al., "Computational Complexity, Protein Structure Prediction and the Levinthal Paradox," in *The Protein Folding Problem and Tertiary Structure Prediction*, Merz, et al., (ed.), Birkhauser, Boston, MA, pp. 433 and 492-495. (1994).
Nooren, I.M.A., et al., "Structural Characterisation and Functional Significance of Transient Protein-Protein Interactions," *Journal of Molecular Biology*, 325(5):991-1018 (Jan. 2003).
Padilla J.E., et al., "Nanohedra: Using Symmetry to Design Self Assembling Protein Cages, Layers, Crystals and Filaments," *Proc. Natl. Acad. Sci.* 98(5):2217-2221 (Feb. 2001).
Pleschberger, M., et al., "Generation of a Functional Monomolecular Protein Lattice Consisting of an S-Layer Fusion Protein Comprising the Variable Domain of a Camel Heavy Chain Antibody," *Bioconjugate Chemistry, American Chemical Society*, 14(2):440-448 (Mar. 2003).
Ringler, P. and Schulz, G.E., "Self-Assembly of Proteins into Designed Networks," *Science*, 302:106-109 (Oct. 3, 2003).
Grant, R.A., et al., "The crystal structure of Dps, a ferritin homolog that binds and protects DNA," *Nature Structural Biology* 5(4):294-303 (Apr. 1998).
Merriam-Webster On-line Dictionary Definition of "fused", Retrieved from the Internet at www.merriam-webster.com, [Retrieved on Oct. 19, 2010].
International Search Report, PCT/GB03/04306, entitled "Protein Lattice," dated Jan. 27, 2004.
Office Action (RR) for U.S. Appl. No. 10/530,795, entitled: "Protein Lattice," dated Jul. 30, 2007.
Office Action for U.S. Appl. No. 10/530,795, entitled: "Protein Lattice," dated Mar. 31, 2008.
Final Office Action for U.S. Appl. No. 10/530,795, entitled: "Protein Lattice," dated Dec. 8, 2008.
Office Action for U.S. Appl. No. 10/530,795, entitled: "Protein Lattice," dated Aug. 18, 2009.
Office Action for U.S. Appl. No. 10/530,795, entitled: "Protein Lattice," dated May 13, 2010.
Office Action for U.S. Appl. No. 10/530,795, entitled: "Protein Lattice," dated Oct. 22, 2010.
Final Office Action for U.S. Appl. No. 12/602,248, entitled: "Protein Layers and Their Use in Electron Microscopy," dated Mar. 17, 2014.

* cited by examiner

SEQUENCE LISTING

```
<160> NUMBER OF SEQ ID NOS: 5

<210> SEQ ID NO 1
<211> LENGTH: 3583
<212> TYPE: DNA
<213> ORGANISM: Artificial Sequence
<220> FEATURE:
<223> OTHER INFORMATION: Derivative of vector pUC19
<220> FEATURE:
<221> NAME/KEY: misc_feature
<222> LOCATION: (709)...(709)
<223> OTHER INFORMATION: n is a, c, g, or t

<400> SEQUENCE: 1
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgggatc catgacagac     240
ttaatccaac gccctcgtcg cctgcgcaaa tctcctgcgc tgcgcgctat gtttgaagag     300
acaacactta gccttaacga cctggtgttg ccgatctttg ttgaagaaga aattgacgac     360
tacaaagccg ttgaagccat gccaggcgtg atgcgcattc cagagaaaca tctggcacgc     420
gaaattgaac gcatcgccaa cgccggtatt cgttccgtga tgacttttgg catctctcac     480
cataccgatg aaaccggcag cgatgcctgg cgggaagatg gactggtggc gcgtatgtcg     540
cgcatctgca agcagaccgt gccagaaatg atcgttatgt cagacacctg cttctgtgaa     600 tacttctc acggtcactg cggtgtgctg tgcgagcatg gcgtcgacaa cgacgcgact     660
ctggaaaatt taggcaagca agccgtggtt gcagctgctg caggtgcana cttcatcgcc     720
ccttccgccg cgatggacgg ccaggtacag gcgattcgtc aggcgctgga cgctgcggga     780
tttaaagata cggcgattat gtcgtattcg accaagttcg cctcctcctt ttatggcccg     840
ttccgtgaag ctgccggaag cgcattaaaa ggcgaccgca aaagctatca gatgaaccca     900
atgaaccgtc gtgaggcgat tcgtgaatca ctgctggatg aagcccaggg cgcaaactgc     960
ctgatggtta aacctgctgg agcgtacctc gacatcgtgc gtgagctgcg tgaacgtact    1020
gaattgccga ttggcgcgta tcaggtgagc ggtgagtatg cgatgattaa gttcgccgcg    1080
ctggcgggtg ctatagatga agagaaagtc gtgctcgaaa gcttaggttc gattaagcgt    1140
gcgggtgcga atctgattt cagctacttt gcgctggatt tggctgagaa gaagattctg    1200
cgtagatctg cgtggcgcca tccgcagttt ggtgggtaag gccgcgactc tagaattcca    1260
```

```
actgagcgcc ggtcgctacc attaccaact tgtctggtgt caaaaataat aggcctacta    1320
gtcggccgta cgggcccttt cgtctcgcgc gtttcggtga tgacggtgaa aacctctgac    1380
acatgcagct cccggagacg gtcacagctt gtctgtaagc ggatgccggg agcagacaag    1440
cccgtcaggg cgcgtcagcg ggtgttggcg ggtgtcgggg ctggcttaac tatgcggcat    1500
cagagcagat tgtactgaga gtgcaccata tgcggtgtga ataccgcac agatgcgtaa     1560
ggagaaaata ccgcatcagg cggccttaag ggcctcgtga tacgcctatt tttataggtt    1620
aatgtcatga taataatggt ttcttagacg tcaggtggca cttttcgggg aaatgtgcgc    1680
ggaacccccta tttgtttatt tttctaaata cattcaaata tgtatccgct catgagacaa    1740
taaccctgat aaatgcttca ataatattga aaaggaaga gtatgagtat tcaacatttc     1800
cgtgtcgccc ttattccctt ttttgcggca ttttgcctc ctgttttgc tcacccagaa      1860
acgctggtga agtaaaaga tgctgaagat cagttgggtg cacgagtggg ttacatcgaa     1920
ctggatctca acagcggtaa gatccttgag agttttcgcc ccgaagaacg ttttccaatg    1980
atgagcactt ttaaagttct gctatgtggc gcggtattat cccgtattga cgccgggcaa    2040
gagcaactcg gtcgccgcat acactattct cagaatgact tggttgagta ctcaccagtc    2100
acagaaaagc atcttacgga tggcatgaca gtaagagaat tatgcagtgc tgccataacc    2160
atgagtgata acactgcggc caacttactt ctgacaacga tcggaggacc gaaggagcta    2220
accgcttttt tgcacaacat gggggatcat gtaactcgcc ttgatcgttg ggaaccggag    2280
ctgaatgaag ccataccaaa cgacgagcgt gacaccacga tgcctgtagc aatggcaaca    2340
acgttgcgca aactattaac tggcgaacta cttactctag cttcccggca acaattaata    2400
gactggatgg aggcggataa agttgcagga ccacttctgc gctcggccct tccggctggc    2460
tggtttattg ctgataaatc tggagccggt gagcgtgggt ctcgcggtat cattgcagca    2520
ctggggccag atggtaagcc ctcccgtatc gtagttatct acacgacggg gagtcaggca    2580
actatgatg aacgaaatag acagatcgct gagataggtg cctcactgat taagcattgg    2640
taactgtcag accaagttta ctcatatata ctttagattg atttaaaact tcatttttaa    2700
tttaaaagga tctaggtgaa gatcctttt gataatctca tgaccaaaat cccttaacgt     2760
gagttttcgt tccactgagc gtcagacccc gtagaaaaga tcaaaggatc ttcttgagat    2820
cctttttttc tgcgcgtaat ctgctgcttg caaacaaaaa aaccaccgct accagcggtg    2880
gtttgtttgc cggatcaaga gctaccaact cttttttccga aggtaactgg cttcagcaga    2940
gcgcagatac caaatactgt ccttctagtg tagccgtagt taggccacca cttcaagaac    3000
tctgtagcac cgcctacata cctcgctctg ctaatcctgt taccagtggc tgctgccagt    3060
ggcgataagt cgtgtcttac cgggttggac tcaagacgat agttaccgga taaggcgcag    3120
cggtcgggct gaacggggg ttcgtgcaca cagcccagct tggagcgaac gacctacacc     3180
gaactgagat acctacagcg tgagctatga gaaagcgcca cgcttcccga agggagaaag    3240
gcggacaggt atccggtaag cggcagggtc ggaacaggag agcgcacgag ggagcttcca    3300
gggggaaacg cctggtatct ttatagtcct gtcgggtttc gccacctctg acttgagcgt    3360
cgatttttgt gatgctcgtc agggggggcgg agcctatgga aaaacgccag caacgcggcc    3420
ttttttacggt tcctggcctt ttgctggcct tttgctcaca tgttctttcc tgcgttatcc    3480
cctgattctg tggataaccg tattaccgcc tttgagtgag ctgataccgc tcgccgcagc    3540
cgaacgaccg agcgcagcga gtcagtgagc gaggaagcgg aag                      3583
```

```
<210> SEQ ID NO 2
<211> LENGTH: 339
<212> TYPE: PRT
<213> ORGANISM: Artificial Sequence
<220> FEATURE:
<223> OTHER INFORMATION: Protomer sequence
<220> FEATURE:
<221> NAME/KEY: VARIANT
<222> LOCATION: (164)...(164)
<223> OTHER INFORMATION: Xaa can be any naturally occurring amino acid

<400> SEQUENCE: 2

Met Thr Met Gly Ser Met Thr Asp Leu Ile Gln Arg Pro Arg Arg Leu
1               5                   10                  15

Arg Lys Ser Pro Ala Leu Arg Ala Met Phe Glu Glu Thr Thr Leu Ser
            20                  25                  30

Leu Asn Asp Leu Val Leu Pro Ile Phe Val Glu Glu Glu Ile Asp Asp
        35                  40                  45

Tyr Lys Ala Val Glu Ala Pro Gly Val Met Arg Ile Pro Glu Lys His
    50                  55                  60

Leu Ala Arg Glu Ile Glu Arg Ile Ala Asn Ala Gly Ile Arg Ser Val
65                  70                  75                  80

Met Thr Phe Gly Ile Ser His Thr Asp Glu Thr Gly Ser Asp Ala
                85                  90                  95

Trp Arg Glu Asp Gly Leu Val Ala Arg Met Ser Arg Ile Cys Lys Gln
            100                 105                 110

Thr Val Pro Glu Met Ile Val Met Ser Asp Thr Cys Phe Cys Glu Tyr
        115                 120                 125

Thr Ser His Gly His Cys Gly Val Leu Cys Glu His Gly Val Asp Asn
    130                 135                 140

Asp Ala Thr Leu Glu Asn Leu Gly Lys Gln Ala Val Val Ala Ala Ala
145                 150                 155                 160

Ala Gly Ala Xaa Phe Ile Ala Pro Ser Ala Ala Met Asp Gly Gln Val
                165                 170                 175

Gln Ala Ile Arg Gln Ala Leu Asp Ala Ala Gly Phe Lys Asp Thr Ala
            180                 185                 190

Ile Met Ser Tyr Ser Thr Lys Phe Ala Ser Ser Phe Tyr Gly Pro Phe
        195                 200                 205

Arg Glu Ala Ala Gly Ser Ala Leu Lys Gly Asp Arg Lys Ser Tyr Gln
    210                 215                 220

Met Asn Pro Met Asn Arg Arg Glu Ala Ile Arg Glu Ser Leu Leu Asp
225                 230                 235                 240

Glu Ala Gln Gly Ala Asn Cys Leu Met Val Lys Pro Ala Gly Ala Tyr
                245                 250                 255

Leu Asp Ile Val Arg Glu Leu Arg Glu Arg Thr Glu Leu Pro Ile Gly
            260                 265                 270

Ala Tyr Gln Val Ser Gly Glu Tyr Ala Met Ile Lys Phe Ala Ala Leu
        275                 280                 285

Ala Gly Ala Ile Asp Glu Glu Lys Val Val Leu Glu Ser Leu Gly Ser
    290                 295                 300

Ile Lys Arg Ala Gly Ala Asp Leu Ile Phe Ser Tyr Phe Ala Leu Asp
305                 310                 315                 320

Leu Ala Glu Lys Lys Ile Leu Arg Arg Ser Ala Trp Arg His Pro Gln
                325                 330                 335

Phe Gly Gly
```

```
<210> SEQ ID NO 3
<211> LENGTH: 9
<212> TYPE: PRT
<213> ORGANISM: Artificial Sequence
<220> FEATURE:
<223> OTHER INFORMATION: Artificial streptavidin ligand

<400> SEQUENCE: 3

Ala Trp Arg His Pro Gln Phe Gly Gly
1               5

<210> SEQ ID NO 4
<211> LENGTH: 127
<212> TYPE: PRT
<213> ORGANISM: Streptomyces avidinii

<400> SEQUENCE: 4

Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 5
<211> LENGTH: 128
<212> TYPE: PRT
<213> ORGANISM: Gallus gallus

<400> SEQUENCE: 5

Ala Arg Lys Cys Ser Leu Thr Gly Lys Trp Thr Asn Asp Leu Gly Ser
1               5                   10                  15

Asn Met Thr Ile Gly Ala Val Asn Ser Arg Gly Glu Phe Thr Gly Thr
            20                  25                  30

Tyr Ile Thr Ala Val Thr Ala Thr Ser Asn Glu Ile Lys Glu Ser Pro
        35                  40                  45

Leu His Gly Thr Gln Asn Thr Ile Asn Lys Arg Thr Gln Pro Thr Phe
    50                  55                  60

Gly Phe Thr Val Asn Trp Lys Phe Ser Glu Ser Thr Thr Val Phe Thr
65                  70                  75                  80

Gly Gln Cys Phe Ile Asp Arg Asn Gly Lys Glu Val Leu Lys Thr Met
                85                  90                  95

Trp Leu Leu Arg Ser Ser Val Asn Asp Ile Gly Asp Asp Trp Lys Ala
            100                 105                 110

Thr Arg Val Gly Ile Asn Ile Phe Thr Arg Leu Arg Thr Gln Lys Glu
        115                 120                 125
```

PROTEIN LAYERS AND THEIR USE IN ELECTRON MICROSCOPY

RELATED APPLICATIONS

This application is a continuation of U.S. application Ser. No. 12/602,248, filed Mar. 26, 2010, which is the U.S. National Stage of International Application No. PCT/GB08/01437, filed on Apr. 23, 2008, published in English, which is a continuation-in-part of U.S. application Ser. No. 11/807,922, filed May 30, 2007, now abandoned, which is a continuation-in-part of U.S. application Ser. No. 10/530,795, filed Nov. 7, 2005, now patented as U.S. Pat. No. 7,989,591, issued on Aug. 2, 2011, which is the U.S. National Stage of International Application No. PCT/GB03/04306, filed on Oct. 8, 2003, published in English. This application claims priority under 35 U.S.C. § 119 or 365 to Great Britain, Application No. 022323.7, filed Oct. 8, 2002. The entire teachings of the above applications are incorporated herein by reference.

SUMMARY

The present invention relates to protein layers which repeat regularly in two dimensions. In one aspect, the protein layers are based on symmetrical oligomer assemblies capable of self-assembly from the monomers of the oligomer assembly. The layers may have pores with dimensions of the order of nanometers to hundreds of nanometers. The protein layers are nanostructures which have many potential uses, for example as a matrix to support molecular entities for electron microscopy, or X-ray crystallography. In another aspect, the invention relates to the use of protein layers for performing electron microscopy.

WO-00/68248 discloses regular protein structures based on symmetrical oligomer assemblies capable of self-assembly. In particular, WO-00/68248 discloses structures formed from protein protomers (referred to as a "fusion protein" in WO-00/68248) comprising at least two monomers (referred to as "oligomerization domains" in WO-00/68248) which are each monomers of a respective symmetrical oligomer assembly. Self-assembly of the monomers into the oligomer assembly causes assembly of the regular structures themselves. Several different types of structures are disclosed, including discrete structures and structures extending in one, two and three dimensions.

In WO-00/68248, the relative orientations of the monomers within the protomers are selected to provide the desired regular structure upon self-assembly. The monomers are fused together through a rigid linking group which is carefully selected to provide the requisite relative orientation of the monomers in the protomer. For example, in the laboratory production reported in WO-00/68248, the selection of the protomer was performed using a computer program to model monomers connected by a linking group in the form of a continuous, intervening alpha-helical segment over a range of incrementally increased lengths. Thus, for example, the lattices suggested in WO-00/68248 having a regular structure repeating in three dimensions are formed from protomers comprising two monomers of respective dimeric or trimeric oligomer assemblies which are symmetrical about a single rotational axis. The relative orientation of the two monomers is selected to provide a specific angle of intersection between the rotational symmetry axis of the two oligomer assemblies. Thus, there is a single fusion between the two oligomer assemblies and the relative orientation of the oligomer assemblies is controlled by careful selection of the linking group providing the fusion. WO-00/68248 only reports laboratory production of protein structures of a discrete cage and a filament extending in one dimension.

It is expected that application of the teaching of WO-00/68248 to protein layers repeating in two dimensions would encounter the following difficulties. Firstly, it is expected that there would be a difficulty in design arising from the requirement to select the relative orientation of the monomers within the protomer appropriate for constructing a layer. This would probably reduce the numbers of types of oligomer assembly available to form a protein layer, and hence make it difficult to identify suitable proteins. Secondly, it is expected that practical difficulties would be encountered during assembly. The structures disclosed in WO-00/68248 rely on the rigidity of the fusion between monomers in protomers which forms the single fusion between oligomer assemblies. WO-00/68248 teaches that the relative orientation of the monomers in the protomers controls the relative orientation of the oligomer assemblies in the resultant structure, so it is expected that flexing of the fusion away from the desired relative orientation would reduce the reliability of self-assembly. It is expected that such a problem would become more acute as the size of the repeating unit increases, thereby providing a practical restriction on the reliable production of lattices with a relatively large pore sizes.

It would be desirable to provide protein layers having a different type of structure in which these expected problems might be alleviated.

According to a first aspect of a present invention, there is provided a protein layer which repeats regularly in two dimensions, the protein layer comprising protein protomers which each comprise at least two monomers genetically fused together, the monomers each being monomers of a respective oligomer assembly, the protomers comprising:

a first monomer which is a monomer of a first oligomer assembly belonging to a dihedral point group of order O, where O equals 3, 4 or 6, and having a set of O rotational symmetry axes of order 2 extending in two dimensions; and a second monomer genetically fused to said first monomer which second monomer is a monomer of a second oligomer assembly having a rotational symmetry axis of order 2 the first monomers of the protomers are assembled into said first oligomer assemblies and the second monomers of the protomers are assembled into said second oligomer assemblies, said rotational symmetry axis of said second oligomer assemblies of order 2 being aligned with one of said set of rotational symmetry axes of order 2 of one of said first oligomer assemblies with two protomers being arranged symmetrically therearound.

As a result of using a second oligomer assembly having a rotational symmetry axis of the same order 2 as the set of O rotational symmetry axes of said first oligomer assembly, the oligomer assemblies are fused with those symmetry axes being aligned and with 2 protomers arranged symmetrically therearound. This means that there is an 2-fold fusion between the first and second oligomer assemblies.

Furthermore the repeating pattern of the protein layer is derived from the arrangement of the rotational symmetry axes of the first oligomer assembly and is not dependent on the relative orientation of the monomers within the protomer. As the first oligomer assembly is dihedral, the set of O symmetry axes of order 2 are coplanar. Therefore the protomers assemble into a layer having the same symmetry as the set of O symmetry axes.

Therefore, protein layers in accordance with the present invention may be designed by selecting oligomers assemblies with appropriate symmetry to build a layer repeating in two dimensions. Protomers are produced comprising monomers of the selected oligomer assemblies fused together. Subsequently, the protomers are allowed to self-assemble under suitable conditions.

To assist in understanding, reference is made to FIG. 1 which illustrates a particular example of a protein layer 1 in accordance with the present invention. FIG. 1 shows only a part of the protein layer 1 which repeats indefinitely in two dimensions. The protein layer 1 assembled from protomers 2. The protein layer 1 has a comprises a first oligomer assembly 3 which in this example belongs to a dihedral point group of order 4 and so has a set of 4 rotational symmetry axes of order 2 (in addition to a single rotational symmetry axis of order 4). Each of the monomers 5 of the first oligomer assembly 3 is fused to a second monomer 6 of a second oligomer assembly 4 which in this example belongs to the dihedral point group of order 2, so having a rotational symmetry axis of order 2. As a result, the second monomers 6 are assembled into the second oligomer assemblies 4 arranged with their rotational symmetry axes of order 2 aligned along the rotational symmetry axes of order 2 of the first oligomer assembly 3, and with a 2-fold fusion between the first and second oligomer assemblies 3 and 4. Thus, the symmetry of the protein layer 1 is the same as the symmetry of the set of four rotational symmetry axes of order 2, in this case rotational symmetry of order 4.

Accordingly, the present invention involves the use of a different class of oligomers assemblies from that used in WO-00/68248. The present invention provides the benefit that one is not restricted by the need to control the relative orientation of the monomers within the protomer. Thus the design of protein structure is assisted in that the relative orientation of the monomers within the protomer is a less critical constraint. Similarly, more reliable assembly of the protein layer is possible, as described in more detail below.

According to other aspects of the present invention, there is provided an individual protomer capable of self-assembly to form such a protein layer, as well as polynucleotides encoding the protomer, vectors and host cells capable of expressing the protomer and methods of making the protomer.

It has been appreciated that a particularly advantageous use of a protein layer which repeats regularly in two dimensions is to perform electron microscopy of a molecular entity. Thus, in accordance with a second aspect of the present invention, there is provided a method of performing electron microscopy of a molecular entity, comprising:

providing a protein layer having a structure which repeats regularly in two dimensions and which supports molecular entities each attached at a predetermined position in the repeating structure of the protein layer; and performing electron microscopy of the protein layer having the molecular entities supported thereon to derive an image.

The method is applicable to any protein layer which repeats regularly in two dimensions, including but not limited to a protein layer in accordance with the first aspect of the present invention.

Thus the protein layer acts as a support for the molecular entities. As the molecular entities each at a predetermined position in the repeating structure of the protein layer, the molecular entities are supported in a regular array. This provides significant advantages in electron microscopy because it allows imaging of large numbers of the individual molecular entities in known positions. This facilitates various forms of data analysis of the derived image, thereby allowing investigation of the structure of the molecular entity.

BRIEF DESCRIPTION OF THE DRAWINGS

The present invention will now be described in more detail by way of non-limitative example with reference to the accompanying drawings, in which.

DETAILED DESCRIPTION

Figure 1:
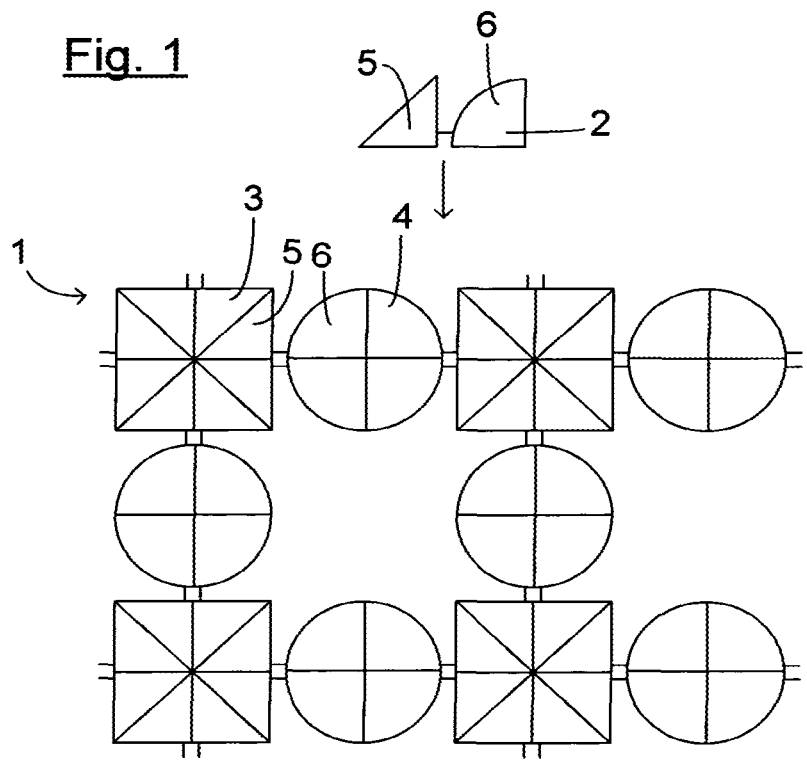
FIG. 1 is a schematic diagram of a protein layer

Protein layers in accordance with the present invention may be designed by selecting oligomer assemblies which, when fused together with rotational symmetry axes of order 2 aligned with each other, produce a repeating unit which is capable of repeating in two dimensions. As the symmetry of the repeating unit, and hence the protein layer as a whole, depends on the symmetry of the oligomer assemblies, this involves a selection of oligomer assemblies having a quaternary structure which provides appropriate symmetries. This is a straightforward task, because the symmetries of oligomer assemblies are generally available in the scientific literature on proteins, for example from The Protein Data Bank; H. M. Berman, J. Westbrook, Z. Feng, G. Gilliland, T. N. Bhat, H. Weissig, I. N. Shindyalov & P. E. Bourne; Nucleic Acids Research, 28 pp. 235-242 (2000) which is the single worldwide archive of structure data of biological macromolecules.

In some cases, the repeating unit repeats in the same orientation across the layer. In other cases, two or more adjacent repeating units together form a unit cell which repeats in the same orientation across the layer, but with the repeating units within a unit cell arranged in different orientations.

Examples of oligomer assemblies which produce structures which repeat regularly in two dimensions are given below.

The first oligomer assembly belongs to a dihedral point group of order O, where O equals 3, 4 or 6 and so has a quaternary structure with rotational symmetry axes extending in two dimensions, including a set of O rotational symmetry axes of order 2 which are coplanar, in addition a single rotational symmetry axis of order O which is perpendicular thereto.

The second oligomer assembly has a quaternary structure with a rotational symmetry axis of the same order 2 as the set of O rotational symmetry axes of said first oligomer assembly. For example, the second oligomer assembly may belong to a dihedral point group of order 2 or to a cyclic point group of order 2. The second oligomer assembly does not have a rotational symmetry axis of order O.

In the assembled first oligomer assembly, inevitably and by definition, there are groups of first monomers arranged symmetrically around each of the set of O rotational symmetry axes of order 2 of the first oligomer assembly. This is because the symmetry results from the identical monomers being so arranged around the rotational symmetry axes.

As a result of the second monomers fused to the first oligomer assembly being arranged symmetrically around one of set of O rotational symmetry axes of order 2 of the first oligomer assembly, it follows that the second oligomer assembly is held with the group of fused second monomers also held symmetrically around that one of the set of O rotational symmetry axes of order 2 of the first oligomer assembly.

In addition, inevitably and by definition, the second monomers also assemble in the second oligomer assembly in a symmetrical arrangement around the rotational symmetry axis of order 2 of the second oligomer assembly. Thus, the result of the second oligomer assembly having a rotational symmetry axis of the same order 2 as the set of O rotational symmetry axes of the first oligomer assembly is that the first and second oligomer assemblies assemble with their symmetry axes of order 2 aligned with one another. It follows from the symmetry of both oligomer assemblies that this is the most stable arrangement. This results in an 2-fold fusion between the first and second oligomer assemblies. In each of the first and second oligomer assemblies, there are 2 monomers arranged around the rotational symmetry axis, each of the monomers being fused within a respective protomer to a monomer of the other oligomer assembly.

As previously mentioned, the set of rotational symmetry axes does not include all the rotational symmetry axes of the first oligomer assembly. Rather the set comprises the rotational symmetry axes of the first oligomer assembly which are of the same order 2 as rotational symmetry axis of the second oligomer assembly.

The particular choice of symmetries of the first and second oligomer assemblies results, on assembly of the protomers into the layer, in the oligomer assemblies being built up with their rotational symmetry axes aligned. Thus, the relative arrangement of the fused oligomer assemblies and hence the protein layer as a whole are therefore derived from arrangements of the rotational symmetry axes of the first oligomer assembly and the second oligomer assembly. In particular, the protein layer has the same symmetry as the set of O rotational symmetry axes of order 2. The symmetry of the protein layer is not dependent on the relative orientation of the monomers within the protomer. In other words, the present invention provides the advantage that the two dimensional repeating pattern of the protein layer may be based solely on the arrangements of the rotational symmetry axes of the oligomer assemblies. This provides advantages in the design of a protein layer by making it easy to select appropriate oligomer assemblies for use in the protein layer. During design, the relative orientation of the monomers within an individual protomer in its unassembled form becomes a much lower constraint than is present in, for example, WO-00/68248.

There are also advantages during self-assembly of the layer. In particular, the formation of a 2-fold fusion between two given oligomer assemblies results in the bond between the two oligomer assemblies being relatively rigid. This reduces relative motion of the oligomer assemblies during the assembly process and assists in reliable formation of the layer with the oligomer assemblies in the correct relative positions.

The form and production of the protomers will now be described. Although the present invention uses protomers which are different in that they comprise different monomers from WO-00/68248, the form and production of the protomers per se, as well as the polynucleotide encoding the protomers, may be as the same as disclosed in WO-00/68248 which is therefore incorporated herein by the reference.

The nature of the monomers themselves will now be described.

The monomers are monomers of oligomer assemblies which are capable of self-assembly under suitable conditions to produce a protein layer. The secondary and tertiary structure of the monomers is unimportant in itself providing they assemble into a quaternary structure with the required symmetry. However, it is advantageous if the protein is easily expressed and folded in an heterologous expression system (for example using plasmid expression vector in $E.\ coli$).

The monomers may be naturally occurring proteins, or may be modified by peptide elements being absent from, substituted in, or added to a naturally occurring protein provided that the modifications do not substantially affect the assembly of the monomers into their respective oligomer assembly. Such modifications are in themselves known for a number of different purposes which may be applied to monomers of the present invention. In other words, the monomer may be a homologue and/or fragment and/or fusion protein of a naturally occurring protein.

The monomer may be chemically modified, e.g. post-translationally modified. For example, it may be glycosylated or comprise modified amino acid residues.

Although the monomers may be fused directly together, preferably the monomers are fused by a linking group of peptide or non-peptide elements. In general, linking two proteins by a linking group is known for other purposes and such linking groups may be applied to the present invention.

Another factor in the selection of appropriate oligomer assemblies is the location and orientation of (a) the termini of the first monomers when arranged in the first oligomer assembly in its natural form (i.e. not fused to a second oligomer assembly) and (b) the termini of the second monomers when arranged in the second oligomer assembly in its natural form (i.e. not fused to the first oligomer assembly). Such information on the arrangement of the termini in the oligomer assembly in its natural form is generally available for oligomer assemblies, for example from The Protein Data Bank referred to above. Ideally, these termini should have the same separation and orientation, because they will be fused together in the assembled protein layer to constitute the 2-fold fusion arranged symmetrically around a rotational symmetry axis. That being said, it is not essential for the separation and orientation to be the same, because any difference may be accommodated by deformation of the monomers near the 2-fold fusion and/or by use of a linking group. Therefore, as a general point, oligomer assemblies should be chosen in which the termini of both oligomer assemblies which are to be fused together in an 2-fold fusion allows formation of the fusion without preventing assembly of the oligomer assemblies and hence the protein layer.

Considering the deformation of the monomers near the 2-fold fusion mentioned above, it is desirable to minimise such deformation which will tend to reduce the reliability of the assembly process. However, if a linking group is fused between the monomers, such deformation may be taken up, at least partially, by the linking group itself. This reduces the deformation of the monomers, thereby increasing the reliability of self-assembly because the linking group does not take part in the assembly process as regards to not being part of the naturally occurring protein. There is a particular advantage of the use of a linking group.

Furthermore, the linking group may be specifically designed to be oriented relative to the first and second monomers in the protomer in its normal form, prior to assembly, to reduce such differences in the position and/or orientation of the termini of the first and second monomers. Using position and orientation of the termini of the first and second monomers in the first and second oligomer assemblies in their natural form which is generally available for oligomer assemblies, as discussed above, it is possible to design an appropriate linking group using conventional modelling techniques.

Typically, the monomers are fused at their end termini. Alternatively, the monomers may be fused at an alternative location in the polypeptide chain so long as the native fold and symmetry of the naturally occurring oligomer assembly remains the same. For example, one of the monomers may be inserted into a structurally tolerant portion of the other monomer, for example in a loop extending out of the oligomer assembly. Also, truncation of a monomer is feasible and may be estimated by structural examination.

Some examples of symmetries for the oligomer assemblies to produce a protein layer which repeats in two dimensions are as follows.

In these examples, the first oligomer assembly belongs to a dihedral point group of order O, where O equals 3, 4 or 6. Hence the first oligomer assembly has a principal rotational symmetry axis of order O and also O rotational symmetry axes of order 2 which all extend perpendicular to the principal rotational symmetry axis. In order to develop a layer extending in two dimensions, the second oligomer assembly is chosen to have a rotational symmetry axis of order 2 to align with the O rotational symmetry axes of order 2 of the first oligomer assembly with a 2-fold fusion between the first and second oligomer assemblies. Therefore, in this case, the O rotational symmetry axes of order 2 constitute the set of rotational symmetry axes of the first oligomer assembly, ie N equals O.

In some classes of protein layer, the protomers are homologous with respect to the monomers, ie there is a single type of protomer within the protein layer. In this case, the second oligomer assembly may belong to a dihedral point group of order 2.

For example, Table 1 represents some simple homologous protomers capable of forming a protein layer.

TABLE 1

Homologous Protomers

| Protomer | M | N | Layer Symmetry |
|---|---|---|---|
| d3d2 | 6 | 2 | P622 |
| d4d2 | 8 | 2 | P422 |
| d6d2 | 12 | 2 | P622 |

In Table 1, each protomer is identified by letters which represent the oligomer assemblies to which the respective monomers of the protomer belong. In particular the letter d represents a dihedral point group and the following number identifies the order of dihedral point group. In the next two columns of Table 1, there is given the number M of first monomers in the first oligomer assembly and the order N of the set of rotational symmetry axes of the first oligomer assembly which in this case is 2. The final column gives the symmetry of the resulting protein layer. In each of these cases, the second oligomer assembly belongs to a dihedral point group of order 2.

Thus it easy to visualise the protein layers. In particular, the first oligomer assembly may be visualised as a node from which the set of O rotational symmetry axes of order 2 extend outwardly in a common plane, perpendicular to the principal rotational symmetry axis of order O. The second oligomer assemblies may be visualised as linear links extending from the node aligned with respective ones of the set of O rotational symmetry axes of order 2 of the first oligomer assemblies. In this way, it is easy to visualise the formation of the layer with pores in the spaces between the oligomer assemblies. Thus it will be seen that the symmetry of the layer derives from the symmetrical arrangement of the set of O rotational symmetry axes of order 2 of the first oligomer assemblies.

In one type of protein layer in which the protomers are homologous with respect to the monomers, the second oligomer assembly is a homologous oligomer assembly. In this case the protein layer consists solely of the protomers.

In another type of such a protein layer in which the protomers are homologous with respect to the monomers, the second oligomer assembly is a hetrologous oligomer assembly of said second monomers and of third monomers. In this case, the protein layer consists of the protomers and in addition the third monomers assembled with said second monomers into said second oligomer assembly.

Thus, the protomer by itself cannot assemble into the entire protein layer. The second monomers of the heterologous oligomer assembly cannot self-assemble into the entire heterologous oligomer assembly in the absence of in the absence of the third monomers of that heterologous oligomer assembly. This provides advantages during manufacture of the protein layers, because first oligomer assemblies may be assembled without assembly of an entire protein layer which might otherwise disrupt the production of the protomer. This allows production in a two-stage process.

A particular heterologous oligomer assembly which may used to advantage as the second oligomer assembly is one comprising monomers which have a binding site capable of binding to biotin or a peptide, and aptamers which are which are capable of binding to said binding site, preferably non-covalently. The aptamers are used as the second monomer of the protomer. The monomers which have a binding site capable of binding to biotin are a third monomer of the protein layer which is not genetically fused within a protomer. On assembly of the second oligomer assembly, the third monomers assemble to each other and the aptamers assemble into the second oligomer assembly by each binding to a respective third monomer.

Figure 2:
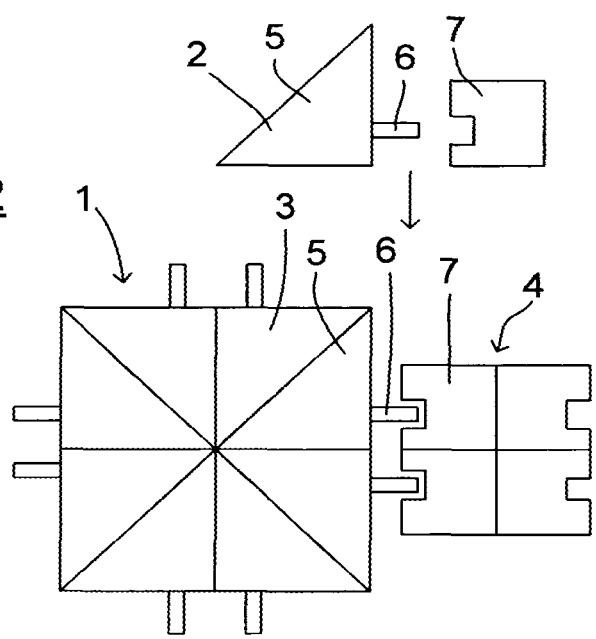
FIG. 2 is a schematic diagram of a protein layer which includes a heterologous oligomer assembly.

This is shown schematically in FIG. 2. which shows an example of a part of the protein lattice 1 including a single second oligomer assembly 4 of this type, the protein lattice otherwise repeating in the same manner as the example shown in FIG. 1. In this example, the first oligomer assembly 3 belongs to a dihedral point group of order 4 and so has a set of four rotational symmetry axes of order 2. Each of the monomers 5 of the first oligomer assembly 3 is fused to a second monomer 6 being an aptamer. The protein lattice 1 further comprises third monomers 7 which are assembled together as part of the second oligomer assembly 4. The second monomers 6 assemble into the second oligomer assembly 4 by each binding to a respective third monomer 7. Thus, in the second oligomer assembly 4, the second monomers 6 are held with the same symmetry as the third monomers 7, but the second monomers 6 are not assembled to each other.

This provides advantages in assisting the formation of the protein lattice. The protein lattice 1 still has a 2-fold fusion between a first oligomer assembly 3 and a second oligomer assembly 4, due to both oligomer assemblies 3 and 4 having a symmetry axis of order 2, as discussed above. However this is achieved without the second monomers 7 themselves needing to assemble to each other. This assists the assembly of the first oligomer assembly 4, in contrast the protein lattice 1 shown in FIG. 1 in which both the first and second oligomer assemblies 3 and 4 need to simultaneously assemble. Instead the third monomers 7 assemble and the second monomers 6 each individually assemble to a respective third monomer 7.

The third monomers typically comprise a binding site. Such a binding site may be capable of binding to peptides or non-peptide moieties. In a preferred embodiment the binding site is capable of binding to biotin. In this case, the third monomer may be of any type having such a binding site, for example streptavidin, avidin or Neutravidin.

The terms "streptavidin", "avidin" or "Neutravidin" as used herein cover variants of these molecules, unless the context requires otherwise. Such variants are typically homologues of the original sequences, i.e. are usually homologues of the sequences shown in SEQ ID NO:4 or SEQ ID NO:5. The variants may be fragments of the original sequences or of homologues of the original sequences. The variant proteins may comprise additional sequences (typically non-streptavidin, non-avidin or non-Neutravidin sequence), and thus be fusion proteins which comprise said original sequences, homologues or fragments.

Preferably the variant sequences retain the structural properties of the original sequences, such as any structural property mentioned herein. Further the variant sequences generally retain the ability to bind biotin and/or a peptide (such as the peptide of SEQ ID NO:3). In one embodiment the variant sequence is capable of being recognised by an antibody which is capable of recognising the original sequence. The variant sequences will of course retain the property of forming a protein layer as described herein.

The second monomers which are aptamers capable of binding to the binding site may be any of a range of peptide tags, including without limitation streptag I, streptag II, or nanotag. Preferred aptamers are peptides which are 7 to 20 amino acids long, for example 9 to 15 amino acids in length. The aptamer may be may have homology with SEQ ID NO. 3, having for example at least 6, 7 or 8 amino acids in common with (i.e. the same as) SEQ ID NO. 3.

In general the first oligomer assembly 1 may be of any type having the required symmetry. One possible example is E. coli ALAD (delta-aminolevulinic acid dehydrogenase). Other criteria for selection of the first oligomer assembly are set out below.

The aptamer may be fused to a terminus of the first monomer. Where the terminus is used, the first oligomer assembly should preferably possess a terminus lying close to a symmetry axis of order 2 (typically within 15 Å).

Alternatively, the aptamer may in general be fused at a position other than the terminus provided that the quaternary structure of the first oligomer assembly properties remains substantially unaffected and provided that the aptamer is one which does not require to be fused to a terminus. For example, Streptag I requires a free C-terminus in order to bind streptavidin. Again it is preferable for apatamer to be fused at a position within the peptide-sequence of the first monomer resulting in the apatamer being located in the assembled oligomer assembly at a position lying close to a symmetry axis of order 2 (typically within 15 Å).

Optionally, there may be a linking group in the protomer between the first monomer and the second monomer which is an apatamer. Typically the linking group might be of length in the range from 1 to 10 amino acids. The linking group might advantageous provide flexibility which assists in the assembly of the lattice For example, in the case that the first monomer is E. coli ALAD and the second monomer is streptag I, it is preferred to provide a linking group of length one or two amino acids.

Optionally, additional protein fusions may be genetically fused to any free termini of the first monomer or third monomer. This might be done to permit functionalisation of the lattice. Specific non-limitative examples of suitable additional proteins are hexa-histidine tags, specific affinity peptides, ankyrin repeats and calmodulin, each of which have been shown in the literature to be capable of genetic fusion to the N-terminus of E. coli ALAD-streptag I without affecting the ability of this assembly to self-assemble into lattices.

In other classes of protein layer, the protomers are heterologous with respect to the monomers i.e. there are two or more types of protomer in the protein layer.

To achieve assembly of two types of protomer, the two types of protomer include different monomers of the same heterologous oligomer assembly which may belong to a cyclic point group of order 2. Thus, the first type of protomer comprises a first monomer which is a monomer of said first oligomer assembly belonging to a dihedral point group of order O, where O equals 3, 4, or 6, genetically fused to a second monomer which is a monomer of the second oligomer assembly, which is the hetrologous oligomer assembly belonging to a cyclic point group of order 2. Furthermore, the second type of protomer comprises a third monomer which is a monomer of that second oligomer assembly. In the second type of protomer, the third monomer is genetically fused to a fourth monomer which is a monomer of a third oligomer assembly, the third oligomer assembly belonging to a dihedral point group of order 2 or O.

Thus when the protomers of the different types are allowed to assemble, the heterologous oligomer assemblies assemble, thereby linking the protomers of the two types. However, a single type of protomer cannot by itself assemble into the entire protein layer. The individual monomers of the heterologous oligomer assembly cannot self-assemble into the entire heterologous oligomer assembly in the absence of the other, different monomers of that heterologous assembly. This provides advantages during manufacture of the protein layers, because each type of protomer may be separately produced and assembled into a respective, discrete component of the unit cell of the repeating pattern, as a result of the monomers of the homologous first oligomer assembly self-assembling, but without assembly of an entire protein layer. This is an advantage of the heterologous protomers, because assembly of the layer may be avoided until the components are brought together. Otherwise assembly of the layer might hinder the production of the protomers themselves. This allows production in a two-stage process.

In the simplest types of protein layer, the first oligomer assembly of both types of protomer is a monomer of a homologous oligomer assembly belonging to a dihedral point group. Thus the individual types of protomer may, for example, Table 2 represents some simple heterologous protomers capable of forming a protein layer.

TABLE 2

| Protomer | Components | Heterologous Protomers | | | | Layer Symmetry |
|---|---|---|---|---|---|---|
| | | 1st Protomer | | 2nd Protomer | | |
| | | M | N | M | N | |
| d3c2A + d3c2A* | D3/D3 | 6 | 2 | 6 | 2 | P622 |
| d4c2A + d4c2A* | D4/D4 | 8 | 2 | 8 | 2 | P622 |
| d6c2A + d6c2A* | D6/D6 | 12 | 2 | 12 | 2 | P622 |
| d3c2A + d2c2A* | D3/D2 | 6 | 2 | 4 | 2 | P622 |
| d4c2A + d2c2A* | D4/D2 | 8 | 2 | 4 | 2 | P622 |
| d6c2A + d2c2A* | D6/D2 | 12 | 2 | 4 | 2 | P622 |

In Table 2, the first column identifies the two types of protomer. Each protomer is identified by letters which represent the oligomer assemblies to which the respective monomers of the protomer belong. In particular the letter d represents a dihedral point group and the letter c represents a monomer of a heterologous oligomer assembly belonging to a cyclic point group. The subscript number again represents the order of the point group. The subscript capital letters A and A* are used to identify the two different monomers of the same heterologous assembly.

In Table 2, the second column identifies the point groups to which the components resulting from the assembly of each type of protomer belongs. A similar notation is used as for the monomers of the protomer, except that capital letters are used to indicate that the point group of the component is being referred to. Thus capital letter D indicates that the component belongs to a dihedral point group and the number gives the order of the point group.

In the next four columns of Table 2, there is given the number M of first monomers in the first oligomer assembly and fourth oligomers in the third oligomer assembly, as well as the order N (=2) of the set of O rotational symmetry axes of the first oligomer assembly and the third oligomer assembly. The final column gives the symmetry of the resulting protein layer.

In all the examples of Table 2, the first oligomer assembly of the first type of protomer belongs to a dihedral point group of order O, where O equals 3, 4 or 6.

In the first three examples of Table 2, the first oligomer assembly of the second type of protomer belongs to a dihedral point group of order L, where L equals O. Thus these three examples have spatially the same arrangement as the three examples of the corresponding homologous protomers in Table 1. In the first three examples of Table 2, the first oligomer assemblies of the two types of protomer may the same oligomer assembly or may be a different oligomer assembly.

In the second three examples of Table 2, the first oligomer assembly of the second type of protomer belongs to a dihedral point group of order L, where L equals 2. These three examples have spatially the same arrangement as the three examples of the corresponding homologous protomers in Table 1, except as follows. Instead of the two dihedral oligomer assemblies of order O being linked by a single cyclic oligomer assembly, the link between the two dihedral oligomer assemblies of order O is extended to be formed by a chain comprising two cyclic oligomer assemblies of order 2 on either side of a dihedral oligomer assembly of order 2. Therefore, it will be seen that the repeating unit of the heterologous oligomer assembly effectively extends the length of the links of the repeating unit between the dihedral oligomer assemblies of order O which may be considered as nodes in the protein layer. Thus, the size of the pores within the protein layer is also increased relative to the use of the corresponding homologous protomers.

The above examples of protein layers are believed to represent the simplest form of protomers capable of forming a protein layer and are preferred for that reason. However, it will be appreciated that other protomers formed from monomers of oligomer assemblies having suitable symmetries will be capable of forming a protein layer. For example, other homologous protomers having larger numbers of monomers than listed in Table 1 will be capable of forming a protein layer. Similarly, other heterologous protomers will be capable of forming a protein layer. These may include two types of protomer having larger numbers of monomers than in the examples of Table 2, or may include more than two types of protomer.

For each of the monomers, there is a large choice of oligomer assemblies having the required symmetry. The present invention is not limited to particular oligomer assemblies, because in principle any oligomer assembly having a quaternary structure with the requisite symmetry may be used. However, as examples Table 3 lists some possible choices of oligomer assemblies of various point groups including those in Tables 1 and 2.

TABLE 3

Example oligomer assemblies

| Point Group | Source | Name of Oligomer Assembly | PDB Code |
|---|---|---|---|
| $P_4(O, 432)$ | E. coli | EpiD | 1G63 |
| | | heavy chain ferritin | 2FHA |
| | E. coli | Dihydrolipoamide succinyltransferase | 1E2O |
| | A. vinelandii | Dihydrolipoamide acetyltransferase | 1EAB |
| | | Mn superoxide dismutase | 1AP5 |
| | P. falciparum | lactate dehydrogenase | 1CEQ |
| $D_3$ | Rat | 6-pyruvoyl tetrahydropterin synthase | 1B66 |
| | E. coli | Amino acid aminotransferase | 1I1L |
| $D_4$ | E. coli | PurE | 1QCZ |
| | Sipunculid worm | Hemerythrin | 2HMQ |
| $D_6$ | S. typhimurium | Glutamine Synthetase | 1F1H |
| $C_{2A} + C_{2A}*$ | Human | Casein Kinase alpha beta chains | 1JWH |
| $C_{3A} + C_{3A}*$ | Coliphate T4 | gp5 + gp27 | 1K28 |
| | HIV | N36 + C34 | 1AIK |
| | Pseudomonas putida | Napthalene 1,2-Dioxygenase | 1NDO |
| $C_{4A} + C_{4A}*$ | Erachiopod | Hemerythrin | N/A |

Thus the present invention provides a protein protomer or plural protein protomers capable of assembly into a protein layer. The monomers of the protomer may be of any length but typically have a length of 5 to 1000 amino acids, preferably at least 20 amino acids and/or preferably at most 500 amino acids.

The invention also provides polynucleotides which encode the protein protomers of the invention. The polynucleotide will typically also comprise an additional sequence beyond the 5 and/or 3 ends of the coding sequence. The polynucleotide typically has a length of at least three times the length of the encoded protomer. The polynucleotide may be RNA or DNA, including genomic DNA, synthetic DNA or cDNA. The polynucleotide may be single or double stranded.

The polynucleotides may comprise synthetic or modified nucleotides, such as methylphosphonate and phosphorothioate backbones or the addition of acridine or polylysine chains at the 3' and/or 5' ends of the molecule.

Such polynucleotides may be produced and used using standard techniques. For example, the comments made in WO-00/68248 about nucleic acids and their uses apply equally to the polynucleotides of the present invention.

The monomers are typically combined to form protomers by fusion of the respective genes at the genetic level (e.g. by removing the stop codon of the 5' gene and allowing an in-frame read through to the 3' gene). In this case the recombinant gene is expressed as a single polypeptide. The genes may, alternatively, be fused at a position other than the end terminus so long as the quaternary structure of the oligomer assembly properties remains substantially unaffected. In particular, one gene may be inserted within a structurally tolerant region of a second gene to produce an in-frame fusion.

The invention also provides expression vectors which comprise polynucleotides of the invention and which are capable of expressing a protein protomer of the invention. Such vectors may also comprise appropriate initiators, promoters, enhancers and other elements, such as for example polyadenylation signals which may be necessary, and which are positioned in the correct orientation, in order to allow for protein expression.

Thus the coding sequence in the vector is operably linked to such elements so that they provide for expression of the coding sequence (typically in a cell). The term "operably linked" refers to a juxtaposition wherein the components described are in a relationship permitting them to function in their intended manner.

The vector may be for example, plasmid, virus or phage vector. Typically the vector has an origin of replication. The vector may comprise one or more selectable marker genes, for example an ampicillin resistance gene in the case of a bacterial plasmid or a resistance gene for a fungal vector.

Promoters and other expression regulation signals may be selected to be compatible with the host cell for which expression is designed. For example, yeast promoters include S. cerevisiae GAL4 and ADH promoters, S. pombe nmt1 and adh promoter. Mammalian promoters include the metallothionein promoter which can be induced in response to heavy metals such as cadmium. Viral promoters such as the SV40 large T antigen promoter or adenovirus promoters may also be used.

Mammalian promoters, such as b-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR).

Another method that can be used for the expression of the protein protomers is cell-free expression, for example bacterial, yeast or mammalian.

The invention also includes cells that have been modified to express the protomers of the invention. Such cells include transient, or preferably stable higher eukaryotic cell lines, such as mammalian cells or insect cells, using for example a baculovirus expression system, lower eukaryotic cells, such as yeast or prokaryotic cells such as bacterial cells. Particular examples of cells which may be modified by insertion of vectors encoding for a polypeptide according to the invention include mammalian HEK293T, CHO, HeLa and COS cells. Preferably the cell line selected will be one which is not only stable, but also allows for mature glycosylation of a polypeptide. Expression may be achieved in transformed oocytes.

The protein protomers, polynucleotides, vectors or cells of the invention may be present in a substantially isolated form. They may also be in a substantially purified form, in which case they will generally comprise at least 90%, e.g. at least 95%, 98% or 99%, of the proteins, polynucleotides, cells or dry mass of the preparation.

The protomers may be prepared using the vectors and host cells using standard techniques. For example, the comments made in WO-00/68248 regarding methods of preparing protomers (referred to as "fusion proteins" in WO-00/68248) apply equally to preparation of protomers according to the present invention.

Assembly of the protein layer from the protomers may be performed simply by placing the protomers under suitable conditions for self-assembly of the monomers of the oligomer assemblies. Typically, this will be performed by placing the protomers in solution, preferably an aqueous solution. Typically, the suitable conditions will correspond to those in which the naturally occurring protein self-assembles in nature. Suitable conditions may be those specifically disclosed in WO-00/68248.

In the case of homologous protomers this results in direct assembly of the protein-layer.

In the case of heterologous protomers, assembly is preferably performed in plural stages. In a first stage, each type of protomer is separately assembled into a respective discrete component. In a second stage, the discrete components are brought together and assembled into the protein layer. Where plural heterologous protomers are used, there may be further stages intermediate the first and second stage in which the respective discrete components are brought together and assembled into larger, intermediate components.

There will now be described a method by which there has been prepared a specific protein layer which is an example of the type shown in FIG. 2

The protomers consisted of a first monomer being E. coli ALAD and a second monomer being streptag I. The third monomer was streptavidin.

The protomers were prepared in an E. coli plasmid vector using standard techniques. The E. coli plasmid vector was a derivative of pUC19 having the sequence SEQ ID NO. 1. The sequence of the protomer is:

TABLE 4

(SEQ ID NO. 2)
MTMGSMTDLIQRPRRLRKSPALRAMFEETTLSLNDLVLPIFVEEEIDDYK

AVEAPGVMRIPEKHLAREIERIANAGIRSVMTFGISHHTDETGSDAWRED

GLVARMSRICKQTVPEMIVMSDTCFCEYTSHGHCGVLCEHGVDNDATLEN

LGKQAVVAAAAGAXFIAPSAAMDGQVQAIRQALDAAGFKDTAIMSYSTKF

ASSFYGPFREAAGSALKGDRKSYQMNPMNRREAIRESLLDEAQGANCLMV

KPAGAYLDIVRELRERTELPIGAYQVSGEYAMIKFAALAGAIDEEKVVLE

SLGSIKRAGADLIFSYFALDLAEKKILRRSAWRHPQFGG

The sequence of Streptag I is:

(SEQ ID NO. 3)
AWRHPQFGG

The sequence of streptavidin (as used in the work described herein) is:

(SEQ ID NO: 4)
MET GLU ALA GLY ILE THR GLY THR TRP TYR ASN GLN

LEU GLY SER THR PHE ILE VAL THR ALA GLY ALA ASP

GLY ALA LEU THR GLY THR TYR GLU SER ALA VAL GLY

ASN ALA GLU SER ARG TYR VAL LEU THR GLY ARG TYR

ASP SER ALA PRO ALA THR ASP GLY SER GLY THR ALA

LEU GLY TRP THR VAL ALA TRP LYS ASN ASN TYR ARG

ASN ALA HIS SER ALA THR THR TRP SER GLY GLN TYR

VAL GLY GLY ALA GLU ALA ARG ILE ASN THR GLN TRP

LEU LEU THR SER GLY THR THR GLU ALA ASN ALA TRP

LYS SER THR LEU VAL GLY HIS ASP THR PHE TRR LYS

VAL LYS PRO SER ALA ALA SER.

For reference the sequence of avidin is:

(SEQ ID NO: 5)
ARKCSLTGKW TNDLGSNMTI GAVNSRGEFT GTYITAVTAT

SNEIKESPLH GTQNTINKRT QPTFGFTVNW KFSESTTVFT

GQCFIDRNGK EVLKTMWLLR SSVNDIGDDW KATRVGINIF

TRLRTQE.

The gene encoding 5-Aminolaevulinic acid dehydratase (ALAD) was amplified from DH5alpha genomic DNA and inserted into the DsRed-Express-streptagI expression vector described above to replace the DsRed-Express gene cassette.

An ALAD-streptagI protomer was then prepared. 0.1 mM IPTG was included in the expression medium. Induction of expression was as follows: a 10 ml overnight culture of the expression strain (in LB broth containing 30 .µg/ml Kanamycin) was diluted 1:100 into fresh LB broth containing 30 m/ml Kanamycin, Cells were grown with shaking at 37° C. to a density corresponding to an $OD_{600}$ of 0.6 and were then induced to express the target protein by the addition of IPTG to a final concentration of 1 mM. The culture was maintained at 37° C. with shaking for a further 3 hours before the cells were harvested by centrifugation (5000 g, 10 min, 4° C.). The cell pellet was resuspended in 20 ml of buffer A (300 mM NaCl, 1 mM EDTA, 50 mM HEPES, pH7.5). Cells were lysed by sonication and the insoluble fraction harvested by centrifugation (25,000 g, 30 min, 4° C.). This fraction was dissolved in 8M urea and centrifuged (25,000 g, 30 min, 4° C.) to remove insoluble particles. The urea solubilised material was concentrated to 16 mg/ml and passed through a 0.22 µm filter. A drop of this material (1 µl) was then directly injected into a larger drop (5 µl) of buffer A.

In general many expression and purification options are available. Another repeatedly successful protocol is as follows:
1. A single colony of BL21 (DE3) Star *E. coli* was transferred from an Luria-Bertani Agar plate to 500 ml of Luria-Bertani medium containing 75 µg/ml ampicillin and 0.1 mM isopropylthio-beta-D-galactopyranoside (IPTG).
2. This culture was incubated with shaking for 18 hrs at 37° C.
3. The culture was harvested by centrifugation (5,000 g, 5 min) and resuspended in 10 ml of buffer "GF" (150 mM NaCl, 50 mM Tris-HCl, 1 mM EDTA, 0.02% sodium azide, pH8.0).
4. Cells were lysed using either sonication, freeze thaw, cells lysis reagents (e.g. "Bugbuster"), or lysozyme and DNAse treatment. These are techniques standard in the art.
5. The insoluble fraction was removed by centrifugation (30,000 g, 30 min).
6. The fusion protein was purified from the soluble fraction using Strep-tactin sepharose (IBA GmbH) according to the manufacturers instructions.
7. Eluted protein was separated from the desthiobiotin contamination that results from the Strep-tactin column by mean of size exclusion chromatography using a superose 6 matrix and buffer GF.
8. Purified protein could be stored at 4° C. for at least 6 months.

Figure 3:
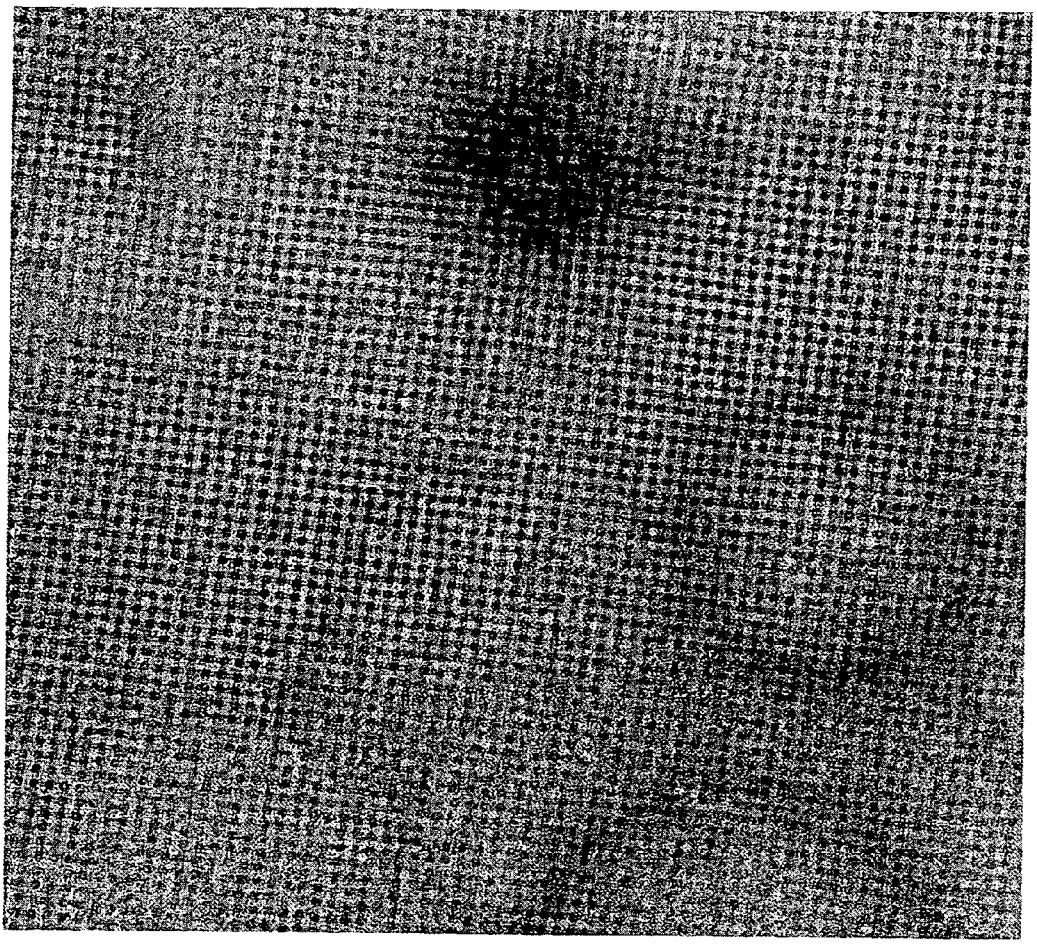
FIG. 3 is an electron micrograph of a specific protein layer which has been prepared.

The purified ALAD-streptag I protomer (~1 mg/ml) was mixed with commercially available core streptavidin in equimolar amounts. Self-assembly commenced immediately and the resultant protein lattices were visualised by means of transmission electron microscopy. FIG. 3 shows a negatively stained transmission electron micrograph of the protein lattice, the unit cell size being 13 nm×13 nm. Image processing of the electron micrographs was performed to enhance the image quality. In particular the electron micrograph was Fourier transformed, filtered using a space group derived filter and averaging, and then reconstructed.

Protein layers in accordance with the present invention have numerous different uses. In general, such uses will take advantage of the regular repeating structure and/or the pores which are present within the structure. Layers in accordance with the present invention may be designed to have pores with dimensions expected to be of the order of nanometers to hundreds of nanometers. Layers may be designed with an appropriate pore size for a desired use.

The highly defined, unusually sized and finely controlled pore sizes of the protein lattices or layers together with the stability of their structures make them ideal for applications requiring microporous materials with pore sizes in the range just mentioned. As one example, the lattices or layers are expected to be useful as a filter element or molecular sieve for filtration or separation processes. In this use, the pore sizes achievable and the ability to design the size of a pore are particularly advantageous.

In another class of use, molecular entities would be attached to the protein layer. Such attachment may be done using conventional techniques. The molecular entities may be any entities of an appropriate size, typically a macromolecular entity, for example proteins, polynucleotides, such as DNA, or non-biological entities. The molecular entities may be a single molecule or a complex of plural molecules. As such, the protein layers are expected to be useful as biological matrices for carrying molecular entities, for example for use in drug delivery, or for crystallizing molecular entities.

Attachment of the molecular entities to the protein layer may be performed in a number of ways.

Some approaches involve "tagging" either or both of the protein protomers (or other component of the layer) or the molecular entities of interest. In this context, tagging is the covalent addition to either or both of the protein protomers (or other component of the layer) or to the target molecular entities, of a structure known as a tag or affinity tag which forms strong interactions with a target structure. Typically, short peptide motifs (e.g. heterodimeric coiled coils such as the "Velcro" acid and base peptides) are used for this purpose. In the case of the protein protomer (or other component of the layer), or a molecular entities which is a protein, this may be achieved by genetically fusing the tag to a component of the protein layer or the molecular entity, that is the expression of a genetically modified version of the protein to carry an additional sequence of peptide elements which constitute the tag, for example at one of its termini, or in a loop region. Alternative methods of adding a tag include covalent modification of a protein after it has been expressed, through techniques such as intein technology.

In one approach, the target structure may be a further tag attached to the other of the protein protomer or target molecular entity, ie both of a component of the layer and target molecular entity include complementary affinity tags for attachment to each other.

In another approach, the target structure may be a part of the protein protomer (or other component of the layer) or target molecular entity, ie one of a component of the layer and target molecular entity has an affinity tags which has an affinity to the other of a component of the layer and target molecular entity. Thus, to attach the molecular entity to the protein layer, a component of the layer may include, at a predetermined position in the protomers, an affinity tag attached to the molecular entity of interest. Alternatively, the molecular entity of interest may have at a predetermined position in the molecular entity, an affinity tag attached to a component of the layer.

When a component of the protein layer is known to form strong interactions with a known peptide sequence, that peptide sequence may be used as a tag to be added to the target molecular entity. Where no such tight binding partner is known, suitable tags may be identified by means of screening. The types of screening possible are phage-display techniques, or redundant chemical library approaches to produce a large number of different short (for example 3-50 amino acid) peptides. The tightest binding peptide elements may be identified using standard techniques, for example amplification and sequencing in the case of phage-displayed libraries or by means of peptide sequencing in the case of redundant libraries.

An alternative approach is for the target molecular entity itself to be expressed as a direct genetic fusion to a component of the layer.

Another alternative approach is to make specific chemical modifications of the lattice in order to provide alternative affinity-based or covalent means of attachment. For example, the site-specific derivitization of accessible sulphydryl groups in the lattice may be used for the incorporation of nitrilo-triacetic acid (NTA) groups which in turn may be used for binding of metal ions and hence histidine rich target proteins.

To attach the molecular entity to the protein layer using an affinity tag on the layer or the molecular entity, the molecular entity may be allowed to diffuse into, and hence become attached to, a pre-formed protein layer, for example by annealing of the bound molecular entity into their lowest energy configurations in the protein layer may be performed using controlled cooling in a liquid nitrogen cryostream. Alternatively, the molecular entities may be mixed with the protomers during formation of the protein layer to assemble with the layer.

In another class of uses, proteins having useful properties could be incorporated as one of the protomers.

A use in which an entity is attached to the protein layer is to perform X-ray crystallography of the molecular entities. In this case, the regular structure of the protein layer allows the molecular entities to be held at a predetermined position relative to a repeating structure, so that they are held in a regular array and in a regular orientation. X-ray crystallography is important in biochemical research and rational drug design.

The protein layer having an array of molecular entities supported thereof may be studied using standard x-ray crystallographic techniques. Use of the protein layer as a support in x-ray crystallography is expected to provide numerous and significant advantages over current technology and protocol for X-ray crystallography, including the following:

(1) Significantly lower amounts of molecule will be required (probably of order micrograms rather than milligrams). This will allow determination of some previously intractable targets.

(2) Use of affinity tags will allow structure determination without the typical requirement for a number of purification steps.

(3) There will be no need to crystallize the molecular entity. This is a difficult and occasionally insurmountable step in traditional X-ray structure determination.

(4) There will be no need to obtain crystalline derivatives for each novel crystal structure to obtain the required phase information. Since the majority of scattering matter will be the known protein layer in each case, determination of the structure may be automated and achieved rapidly by a computer user with little or no crystallographic expertise.

(5) The complexes of a protein with chemicals (substrates/drugs) and with other proteins can be examined without requiring entirely new crystallization conditions.

(6) The process is expected to be extremely rapid and universally applicable, which will provide enormous savings in time and costs.

For use in catalysing biotransformations, enzymes may be attached to the protein layer, or incorporated in the protein layer.

For use in data storage, it may be possible to attach a protein which is optically or electronically active. One example is Bacteriorhodopsin, but many other proteins can be used in this capacity. In this case, the protein layer holds the attached protein in a highly ordered array, thereby allowing the array to be addressed. The protein layer might overcome the size limitations of existing matrices for holding proteins for use in data storage.

For use in a display, it may be possible to attach a protein which is photoactive or fluorescent. In this case, the protein layer holds the attached protein in a highly ordered array, thereby allowing the array to be addressed for displaying an image.

For use in charge separation, a protein which is capable of carrying out a charge separation process may be attached to the protein layer, or incorporated in the protein layer. Then the protein may be induced to carry out the separation, for example biochemically by a "fuel" such as ATP or optically in the case of a photoactive centre such as chlorophyll or a photoactive protein such as rhodopsin. A variety of charge separation processes might be performed in this way, for example ion pumping or development of a photo-voltaic charge.

For use as a nanowire, a protein which is capable of electrical conduction may be attached to the protein layer, or incorporated in the protein layer. Using an anisotropic protein layer, it might be able to provide the capability of carrying current in a particular direction.

For use as a motor, proteins which are capable of induced expansion/contraction may be incorporated into the protein layer.

The protein lattices may be used as a mould. For example, silicon could be diffused or otherwise impregnated into the pores of the protein lattice, thus either partially or completely filling the lattice interstices. The protein material comprising the original lattice may, if required, then be removed, for example, through the use of a hydrolysing solution.

Another use in which an entity is attached to the protein layer is to perform electron microscopy of the molecular entities. This may be performed to determine the structure of the entities. The entities may be of any type including a macromolecule (e.g. a protein or DNA) or a macromolecular complex (e.g. a complex of a macromolecule with one or more other molecular species).

There will first be described known electron microscopy techniques by way of background.

Figure 4:
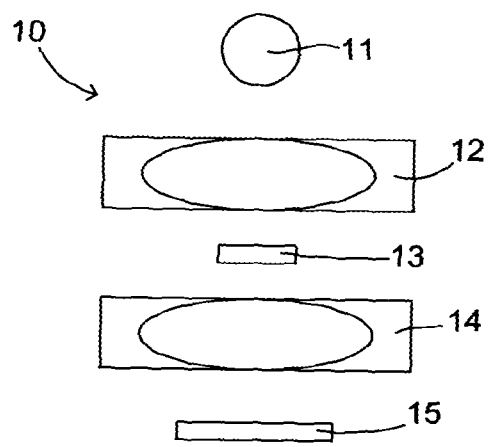
FIG. 4 is a schematic diagram of an transmission electron microscope.

FIG. 4 schematically shows a transmission electron microscope 10 arranged as follows. An electron source 11 produces electrons. An objective lens system 12 directs a beam of electrons from the source 11 onto a sample 13. An imaging lens system 14 directs electrons transmitted through the sample 13 onto a sensor 15 which produces an image. The image may be a focussed image or may be a diffraction pattern, the latter being useful where the entity is presented in a regular array (e.g. tubes of molecules, 2D crystals, or helical arrays). Information from multiple images, corresponding to multiple different views of the molecular species, may be subsequently combined to produce a 3D reconstruction.

Sample preparation and presentation within the microscope is performed as follows. In practise, samples 13 are presented to the electron beam within the sample holder of an electron microscope. Samples 13 are generally mounted on a copper grid. This may have been coated with a thin layer of deposited carbon that may in turn be either continuous across the holes of the grid, or may be deliberately incomplete so as to leave holes in which the sample floats (a "lacey" carbon layer).

Details of the sample mounting protocol depend on whether or not the sample is to be visualised under cryoconditions.

For cryo conditions, the sample 13 may be introduced into a medium that is augmented with a cryoprotectant agent so as to minimise the tendency to form ice at low temperatures. Examples of cryoprotectant agents include glucose and trehalose. In addition, a contrast-enhancing constituent may be added to the sample 13 environment. An example of a contrast enhancing agent is tannin. After cryoprotection, the sample 13 is introduced onto the (possibly coated) copper grid, excess sample and embedding medium are withdrawn by blotting so as to produce a sample 13 no thicker than 1000 Å, and the grid is introduced into an environment at cryotemperatures (<200K). The speed of cooling is an important factor in avoiding the formation of ice and consequent sample damage during freezing. Rapid cooling may be achieved by plunging the sample 13 into liquid nitrogen, into a stream of gaseous nitrogen at temperatures below 120K, or into a bath of a less volatile liquid (such as propane) at cryo temperatures. Mechanical stages may be used to ensure a rapid and reproducible introduction of the copper grid into the freezing environment.

Where samples 13 are not to be presented in vitreous frozen solution (i.e. under non-cryo conditions), a solution of the substance to be imaged is introduced onto a carbon-coated copper grid, a period of time is left for sample to adsorb to the carbon layer, and then excess sample and solution are withdrawn by blotting. To enhance the contrast of images, and to minimise the deleterious consequences of radiation damage, the sample 13 may then be stained. Since biological samples demonstrate intrinsically low scattering, the stains used are generally themselves electron dense, and hence strongly scattering. Thus the stains used are generally "negative stains": the images recorded are dark where the stain is, and are lighter in regions from which stain is excluded by the presence of the sample. Uranyl acetate is an example of a negative stain.

Data collection is performed as follows.

In the case of deriving a focussed image, images are in fact recorded away from perfect focus. While this is done to generate contrast in the image, it results in a degradation of the image. Specifically, Fourier terms calculated from the image are modulated by a "Contrast Transfer Function" (CTF), which modulates the amplitudes of Fourier terms in a manner that is a function of the corresponding scattering angle. Corrected Fourier terms can generally be recovered by appropriate scaling once the extent of defocus and astigmatism have been characterised. At a given defocus, the CTF will adopt a value of zero for Fourier terms corresponding to particular scattering angles. These terms cannot, therefore, be recovered by post processing. To fill in the corresponding holes in reciprocal space, images are recorded at a range of defocuses, so that Fourier terms that are modulated to (or close to) zero in an image recorded at one defocus will have a measurable amplitude at another defocus.

Inelastic interaction of electrons with the sample results in deposition of energy that, in turn, causes damage to the sample. This damage degrades the structure of the molecules within the sample. For this reason, images and diffraction patterns are recorded using a relatively low dose of electrons. This experimental limitation means that there is a relatively poor signal to noise ratio in the recorded images of each molecular species captured within the field of view of an image. This translates to each image carrying relatively low resolution information about the structure of sample. In general, enhancement of the signal to noise is achieved by effectively averaging the images of multiple molecules that are observed in the same (or similar) orientations with respect to the electron beam.

Each image approximates to a projection of the electron density (or more precisely the potential) distribution of the molecular species. Hence, a single image of a single molecule does not contain sufficient information to infer the 3D structure of that molecule. Therefore, images have to be recorded from the sample in multiple orientations with respect to the beam.

For periodic structures, Fourier components can be measured directly by recording the diffraction pattern, rather than an image of the sample. This approach avoids the complication of modulation by the CTF although other characteristics of the experiment and of the instrument must still be corrected for in post-processing. For periodic samples (e.g. 2D crystals or helical arrays), scattering becomes concentrated into discrete directions that are characteristic of the size and shape of the repeated unit (i.e. the unit cell), giving rise to diffraction spots in the scattering pattern, rather than a continuous scattering function. This process of "Bragg amplification" makes for readily recordable signals. A further advantage of recording the diffraction pattern is that the intensities of the scattered pattern (i.e. that property which is recorded) are independent of global motions of the sample during the exposure. Such motions can be caused by thermal fluctuation as well as specific heating and charging of the sample caused by the electron beam. A disadvantage of recording the scattered pattern rather than focussed electrons (i.e. a diffraction pattern rather than an image) is that recording of the scattered pattern loses phase information for the Fourier terms. At the same time, local imperfections in a can be corrected if an image thereof is collected, but not (trivially) if a diffraction pattern is collected.

In the case of electron tomography, a single example of the species to be visualised is imaged with extremely low dose at a range of orientations. Hence a single molecular species is imaged. This addresses a potential criticism of other approaches: each representative molecule of a sample might be subtly different, which makes both the averaging of multiple images and 3D reconstruction inappropriate. It has the disadvantage that the electron dose that can be tolerated by a single species is spread over imaging in multiple orientations: this ultimately limits the resolution of 3D reconstruction that can be achieved.

Data analysis is performed as follows.

The protocol used to analyse data from electron microscopy depends primarily on whether the sample is periodic (i.e. 2D crystalline or presented in a helical array), or aperiodic, i.e. presented as isolated particles which may or may not have local rotational symmetry, but which lack significant translational symmetry. In both cases, where image (rather than diffraction data) have been collected, the defocus and astigmatism of the sample are identified by analysis of the intensity distribution of Fourier transformed regions of the image. Based on these values, which may vary across the image, an appropriate correction can be calculated to compensate for CTF effects.

One type of data analysis is single particle reconstruction. This allows reconstruction of a three-dimensional (3D) image from images of individual entities, as follows.

For non-periodic samples, images (rather than diffraction patterns) are recorded. Analysis begins with locating samples on the recorded image. For unstained biological molecules this presents a significant problem: the inherently low signal-to-noise ratio means that molecules may not be apparent against background. Even if they are visible such molecules may be so poorly imaged as to preclude the characterisation of their orientation compared to other images of the same molecular species. This problem is made worse where the species to be visualised is small. In practise, it is not readily possible to apply conventional EM to non-crystalline samples of macromolecules (or macromolecular complexes) with a combined molecular weight less that ~125 kDa.

After locating multiple molecular species to assemble a "dataset" of (noisy) images, the next stage is classification. In this step, images of the molecular species are grouped, so that those that represent similar views are associated with each other. Particularly where a carbon support has been used, there may be a limited set of such views present in the dataset. Images of particles that fall within such clusters are averaged to provide "class averages". The relative orientations of a set of class averages is determined by means of a "common lines" or similar approach. Ultimately, this allows the information from multiple different views to be assembled in reciprocal space so as to permit 3D reconstruction.

Another type of data analysis is two-dimensional (2D) crystallographic analysis. This is applicable to periodic samples. Data may have been collected as images or as diffraction patterns.

In images of a crystalline lattice, recognition of the geometry and location of the lattice provides a readily exploited means of predicting the location of the multiple copies of the species to be imaged. Averaging can be performed either in real space (where individual unit cell images are summed) or in reciprocal space. In the latter approach, the image is Fourier transformed to produce a set of diffraction spots that result from scattering by that part of the image which has a periodic character, i.e. by the ordered array of molecules. The rest of the scattering (i.e. that intensity which does not fall at the position of diffraction spots) comes from background and noise. The multiple unit cells in the field of view can therefore be averaged by setting all off-peak intensities to zero and carrying out a further Fourier transformation. This process is called Fourier filtering. Both real space averaged and Fourier Filtered images can be enhanced by a process of "unbending" In this process, local distortions of the lattice can be identified (generally by an autocorrelation method), and used to correct the image to generate a picture that would prevail if the lattice were not subject to any local distortion.

Diffraction patterns of the crystalline lattice can be used to measure directly the amplitudes of Fourier components. Phases for these terms can be established only using methods analogous to those used in protein crystallography. These include isomorphous replacement (IR), molecular replacement (MR), and density modification (DM). For IR, diffraction has to be measured before and after the addition (or substitution) of a part of the structure. For MR, a known structure or electron density distribution can be used to calculate phases for the unknown structure. For DM, phases for low resolution terms must be available (e.g. from analysis of images as above), and phasing of high resolution terms is achieved by iterative imposition of averaging and solvent flattening, including increasingly high resolution terms into the process as phase is extended.

The disposition of the crystal with respect to the beam can be inferred from the apparent geometry of diffraction spots, which may either be recorded directly or calculated by Fourier transformation of an image, provided that the geometry of the repeating unit in the crystal (the unit cell geometry) is known. Where the structure of a significant part of the lattice is known, a calculated image of this part of the lattice can also be used to assess the orientation of the lattice in an experimentally recorded image. Thus information from multiple images in multiple orientations, collected at multiple tilt angles can readily be combined to carry out 3D image reconstruction.

The application to imaging of molecular entities supported on a protein lattice will now be described. Benefits are achieved because the entities are each supported at a predetermined position in the repeating structure of the protein layer.

Figure 5:
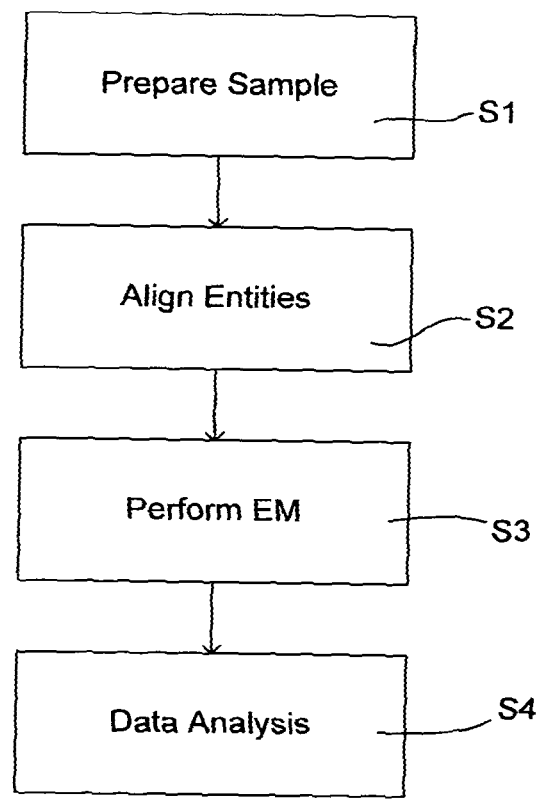
FIG. 5 is a flowchart of a method of performing electron microscopy.

There may be used a conventional transmission electron microscope 10, for example as shown in FIG. 4. Imaging is performed using the method shown in FIG. 5.

First in step S1, there is prepared a protein lattice having the molecular entities attached thereto. This is done using the techniques described above. A sample 13 for the transmission electron microscope 10 is prepared with the protein lattice using standard procedures, as discussed above.

Two approaches for attaching the entity to the protein layer are as follows.

In the first approach, the entity is added to a solution (or suspension) containing the protein layer. Thus the entities attach to the layer in solution. The resultant layer is then subjected to sample preparation as described above for either cryo electron microscopy or for non-cryo electron microscopy, either with or without staining In the second approach, the protein layer is first deposited onto the carbon layer of a coated copper grid to form the sample holder of the electron microscope 10. The entity is introduced subsequently. In this case, a suspension of the protein lattice is placed on the carbon-coated grid, adsorption is allowed to occur, excess crysalin and surrounding solution are removed, and a solution of the target species is introduced. After an incubation in which binding of the target to the crysalin occurs, excess target and surrounding solution is removed. Subsequent sample preparation is as described above for either cryo electron microscopy or for non-cryo electron microscopy For optimal resolution in the structure of the molecular entity, it is preferable for the molecular entities to be aligned with identical orientations with respect to every axis. In step S2 which is optional, the molecular entities are aligned with respect to the protein lattice.

Two possible methods of molecular alignment which may be implemented, either independently or in combination, are as follows.

A first alignment method is to apply an electric field with a vector parallel to the principal symmetry axis of the "first" protein layer component in order to align the molecular entities by virtue of their intrinsic or induced dipoles.

A second alignment method takes advantage of polar and/or hydrophobic interactions between molecular entities and the protein layer through a process of thermal annealing during which the target molecules are slowly cooled to identical minimum energy conformations.

In step S3, imaging is performed to derive an image. Such data collection is conducted using standard protocols, for example as described above for conventional EM. By way of example images may be collected at a series of defocus steps and also employing the tilt-stage of the microscope to image the lattice through a range of angles. Where orientation of the target molecules has been successful, a series of electron diffraction images may also be usefully collected.

In step S4, data analysis of the images is performed. A variety of data analysis techniques may be applied, as follows.

Where it has been possible to impose an approximately common orientation of each bound target molecule with respect to the underlying lattice, a 2D crystallographic data analysis may be performed, as described above. This allows a 3D reconstruction of the target molecule to be derived.

Single particle image reconstruction tools can also theoretically be applied to image reconstruction of 2D periodic arrays, and where this provides improved image reconstruction, that approach is also taken to image protein layers and attached molecular entities. Hybrid methods, whereby some computational techniques of 2D crystallography are combined with computational techniques of single particle image analysis, are also used where this is suitable.

Where it has not been possible to impose an approximately common orientation of each bound target molecule, a combination of the methods outlined above for single particle 3D reconstruction and 2D crystallography are applied. In this combination, the components of the protein lattice itself are identified and subtracted from the image.

The components of the protein lattice may be derived as described above from an analysis of one or more recorded images of a protein layer and attached molecular entities. Alternatively, the components of the protein lattice may be derived from a reference image acquired separately or being a stored image acquired previously.

This allows the lattice components of each image are identified to be removed. The resulting difference image is an image of the entities in isolation that would have been recorded if the entities were disposed in space at positions having the same repeating pattern as the structure of the protein layer, albeit in a partially random orientation.

Thereafter single particle reconstruction is performed, as described above. This process is expedited by the fact that the protein layer will be found at readily predicted positions on the image, as a consequence of their binding to known locations on the protein layer, the location and orientation of which is readily identified. The subtraction of the reference image effectively accomplishes the first step of single particle 3D reconstruction (particle picking) as described above. Similarly, a degree of alignment of the molecules is likely to apply and contributes to particle classification.

Variants

Homologues of protein sequences are referred to herein. Such homologues typically have at least 70% homology, preferably at least 80, 90%, 95%, 97% or 99% homology, for example over a region of at least 15, 20, 30, 100 more contiguous amino acids. The homology may be calculated on the basis of amino acid identity (sometimes referred to as "hard homology").

For example the UWGCG Package provides the BEST-FIT program which can be used to calculate homology (for example used on its default settings) (Devereux et at (1984) Nucleic Acids Research 12, p 387-395). The PILEUP and BLAST algorithms can be used to calculate homology or line up sequences (such as identifying equivalent or corresponding sequences (typically on their default settings), for example as described in Altschul S. F. (1993) *J Mol Evol* 36:290-300; Altschul, S, F et at (1990) *J Mol Biol* 215:403-10.

Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differ by at least 2, 5, 10, 20 or more mutations (which may be substitutions, deletions or insertions of amino acids). The homologous sequence typically differ by at most 5, 10, 20 or more mutations (which may be substitutions, deletions or insertions of amino acids). Typically, up to 40% of the amino acids of the sequence are mutated. These mutation may be measured across any of the regions mentioned above in relation to calculating homology. The substitutions are preferably conservative substitutions. These are defined according to the following Table. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

What is claimed is:

1. A method of performing electron microscopy of a molecular entity supported on a protein layer, the method comprising:
providing the protein layer and a plurality of the molecular entity,
the protein layer: (a) supporting the plurality of the molecular entity, (b) having a structure which repeats regularly in two dimensions to form a repeating structure and (c) comprising protein protomers which each comprise at least two monomers genetically fused together, the monomers each being monomers of a respective oligomer assembly,
the protomers comprising:
a first monomer which is a monomer of a first oligomer assembly belonging to a dihedral point group of order O, where O equals 3, 4 or 6, and having a set of O rotational symmetry axes of order 2 extending in two dimensions; and
a second monomer genetically fused to said first monomer which second monomer is a monomer of a second oligomer assembly having a rotational symmetry axis of order 2,
the first monomers of the protomers being assembled into said first oligomer assemblies and the second monomers of the protomers being assembled into said second oligomer assemblies, said rotational symmetry axis of said second oligomer assemblies of order 2 being aligned with one of said set of rotational symmetry axes of order 2 of one of said first oligomer assemblies with two protomers being arranged symmetrically therearound,
each of the plurality of the molecular entity being attached to the protein layer at a predetermined position in the repeating structure of the protein layer; and
performing electron microscopy of the plurality of the molecular entity supported on the protein layer to derive an image.

2. The method according to claim 1, wherein said step of providing the protein layer and the plurality of the molecular entity comprises making the protein layer and subsequently attaching the plurality of the molecular entity thereto.

3. The method according to claim 1, further comprising the step of attaching the plurality of the molecular entity to the protein layer in solution to form the recited protein layer and the plurality of the molecular entity.

4. The method according to claim 1, further comprising, prior to the step of performing electron microscopy, aligning the plurality of the molecular entity with respect to the protein layer.

5. The method according to claim 4, wherein the step of aligning the plurality of the molecular entity with respect to the protein layer comprises applying an electric field to the protein layer.

6. The method according to claim 4, wherein the step of aligning the plurality of the molecular entity with respect to the protein layer comprises cooling the protein layer to a minimum energy state.

7. The method according to claim 1, further comprising performing data analysis of the derived image.

8. The method according to claim 7, wherein the data analysis is a two-dimensional crystallographic data analysis.

9. The method according to claim 7, wherein the data analysis comprises identifying, in the derived image, image data corresponding to the protein layer and subtracting the identified image data from the derived image to obtain an image of the plurality of the molecular entity, and performing a single particle reconstruction of the obtained image of the plurality of the molecular entity.

10. The method of claim 1, wherein the second oligomer assembly belongs to a dihedral point group of order 2 or to a cyclic point group of order 2.

11. The method of claim 1, wherein the protomers are homologous with respect to the monomers.

12. The method of claim 11, wherein said second oligomer assembly belongs to a dihedral point group of order 2.

13. The method of claim 11, wherein the second oligomer assembly is a heterologous oligomer assembly of said second monomers and of third monomers, said protein layer further comprising said third monomers assembled with said second monomers into said second oligomer assembly.

14. The method of claim 13, wherein the third monomers are monomers which have a binding site capable of binding to biotin or a peptide, and said second monomers are aptamers which are capable of binding to said binding site.

15. The method of claim 14, wherein said third monomers are streptavidin.

16. The method of claim 14, wherein said second monomers are Streptag I (SEQ ID NO. 3).

17. The method of claim 1, wherein the protomers are heterologous with respect to the monomers.

18. The method of claim 17, wherein the protein layer comprises protein protomers of two types,
the first type of protomer comprising a first monomer which is a monomer of said first oligomer assembly belonging to a dihedral point group of order O, where O equals 3, 4, or 6, genetically fused to a second monomer which is a monomer of said second oligomer assembly, said second oligomer assembly being a heterologous oligomer assembly belonging to a cyclic point group of order 2, and
the second type of protomer comprising a third monomer which is a monomer of said second oligomer assembly, genetically fused to a fourth monomer which is a monomer of a third oligomer assembly, said third oligomer assembly belonging to a dihedral point group of order 2 or O.

19. The method of claim 18, wherein said oligomer assembly belongs to a dihedral point group of order O, said third oligomer assembly being the same as said first oligomer assembly.

20. The method of claim 1, wherein each of said monomers of said respective oligomer assemblies either is a naturally occurring protein or is based on a naturally occurring protein with peptide elements being absent from, substituted in, or added to the naturally occurring protein without substantially affecting assembly of monomers of said respective oligomer assembly.

21. The method of claim 1, wherein, in said protomers, said monomers are genetically fused via a linking group.

22. The method of claim 21, wherein the linking group is oriented relative to the first and second monomers in the protomer in its normal form prior to assembly to reduce any difference in the assembled layer in either or both of the position and orientation of (a) the termini of said first monomers in their arrangement in said first oligomer assembly in its natural form symmetrically around said one of said set of rotational symmetry axes of order N of said first oligomer assembly, and (b) the termini of said second monomers in their arrangement in said second oligomer assembly in its natural form symmetrically around said rotational symmetry axis of order N of said second oligomer assembly.

23. The method of claim 1 wherein a component of the protein layer has an affinity tag, the molecular entities being attached to respective affinity tags.

24. The method of claim 1, wherein the molecular entity comprises a protein having a peptide affinity tag attached to a component of the protein layer.

25. The method of claim 1, wherein the molecular entity comprises a protein, and both of a component of the protein layer and the molecular entity have respective affinity tags attached to each other.

26. The method of claim 1, wherein the molecular entities are genetically fused within a component of the protein layer.

* * * * *